United States Patent
Stankus et al.

(10) Patent No.: US 9,907,695 B2
(45) Date of Patent: Mar. 6, 2018

(54) OPHTHALMIC SHUNT AND METHOD

(71) Applicant: Abbott Cardiovascular Systems Inc., Santa Clara, CA (US)

(72) Inventors: John Stankus, Campbell, CA (US); James Su, San Marino, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 136 days.

(21) Appl. No.: 15/008,279

(22) Filed: Jan. 27, 2016

(65) Prior Publication Data
US 2016/0158060 A1    Jun. 9, 2016

Related U.S. Application Data

(62) Division of application No. 13/893,055, filed on May 13, 2013, now abandoned.

(51) Int. Cl.
*A61M 31/00* (2006.01)
*A61F 9/00* (2006.01)

(52) U.S. Cl.
CPC ................... *A61F 9/0017* (2013.01)

(58) Field of Classification Search
CPC ................................... A61F 9/0017
See application file for complete search history.

(56) References Cited

U.S. PATENT DOCUMENTS

| | | | |
|---|---|---|---|
| 2009/0306608 A1* | 12/2009 | Li | A61F 9/0017 604/294 |
| 2011/0098686 A1* | 4/2011 | Varner | A61F 9/0017 604/890.1 |
| 2014/0276329 A1* | 9/2014 | Urbaniak | A61F 9/0017 604/8 |
| 2014/0358125 A1* | 12/2014 | de Juan, Jr. | A61K 9/0051 604/521 |

* cited by examiner

*Primary Examiner* — Rebecca E Eisenberg
(74) *Attorney, Agent, or Firm* — Squire Patton Boggs (US) LLP

(57) ABSTRACT

An ophthalmic shunt includes a seal or septum through which multiple injections of the therapeutic agent can be made as needed, thereby avoiding repeated injury to the sclera. The therapeutic agent is temporarily carried in a tube connected to the septum. The therapeutic agent release may be rapid or sustained over a period of time.

20 Claims, 7 Drawing Sheets

OPHTHALMIC SHUNT AND METHOD

CROSS-REFERENCE TO RELATED APPLICATION

This application is a divisional application Ser. No. 13/893,055, filed May 13, 2013, which application is hereby incorporated by reference.

FIELD OF THE INVENTION

The present invention relates to an implantable medical device and method, and more particularly, to an ophthalmic shunt and method for delivering a therapeutic agent into the eye.

BACKGROUND

Diseases of the posterior segment of the eye are conventionally treated by direct injection of a therapeutic agent. Treatment of diseases often requires repeated injections, which means repeated injury to the eye. Repeated injury to the eye increases the risk of complications, such as infection, endophthalmitis, high intraocular pressure, glaucoma, cataract, retinal detachment and bleeding, and insufficient wound healing.

What is needed is a device and method for mitigating the risk of such complications. What is needed is a device and method for providing a safe compartmental portal for one or multiple injections of therapeutic agent into the eye.

SUMMARY OF THE INVENTION

Briefly and in general terms, the present invention is directed to an ophthalmic shunt and method.

In aspects of the present invention, an ophthalmic shunt comprises a tube having an inlet aperture, and a septum adjacent the inlet aperture, the septum forming a resilient seal against fluid flow, the septum configured to be pierced by a needle.

In further aspects, the septum is configured to autonomously close an aperture formed by a needle having pierced the septum and having been withdrawn from the septum.

In aspects of the present invention, a method comprises introducing a therapeutic agent through a septum attached to a tube of an ophthalmic shunt implanted through the sclera of an eye, and allowing the therapeutic agent to exit from the tube and into the eye.

In further aspects, the introducing includes piercing the septum with a needle through which the therapeutic agent flows into the tube.

In aspects of the present invention, an implantable ophthalmic shunt comprises a reservoir configured to carry a therapeutic agent and configured for implantation between the sclera of an eye and a Tenon's capsule surrounding the eye, and a conduit configured to be implanted through the sclera and to transport the therapeutic agent from the reservoir and into the eye.

In aspects of the present invention, a method comprises placing a conduit through the sclera of an eye, and placing a reservoir between the sclera and a Tenon's capsule surrounding the eye, wherein the reservoir is configured to contain a therapeutic agent and the conduit is configured to transport the therapeutic agent from the reservoir and into the eye.

The features and advantages of the invention will be more readily understood from the following detailed description which should be read in conjunction with the accompanying drawings.

BRIEF DESCRIPTION OF THE DRAWINGS

It is to be understood that the figures are not to scale.

DETAILED DESCRIPTION OF EXEMPLARY EMBODIMENTS

All values for dimensional values and ranges in this specification are exemplary.

Figure 1A:
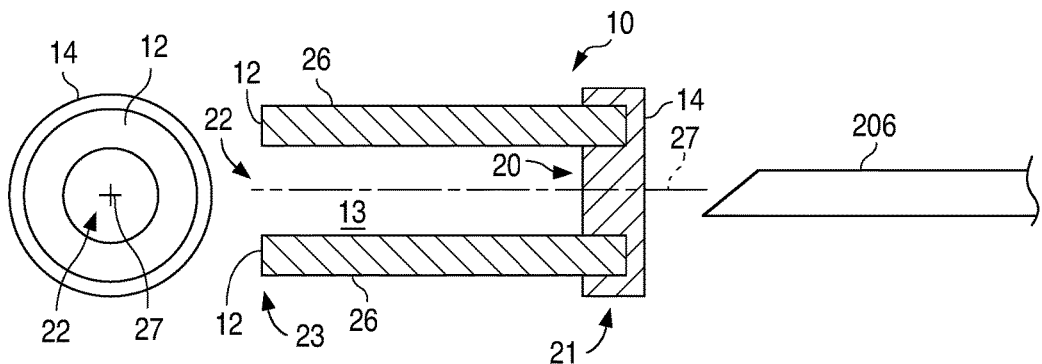
FIG. 1A is a diagram showing an end view and a side cross-sectional view of an ophthalmic shunt and showing a needle outside the shunt.
Figure 1B:
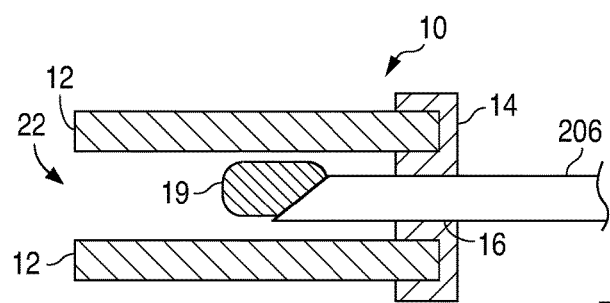
FIG. 1B is a side cross-sectional view of the shunt showing the needle piercing a septum of the shunt and delivering a therapeutic agent into the shunt, the needle forming an aperture in the septum.
Figure 1C:
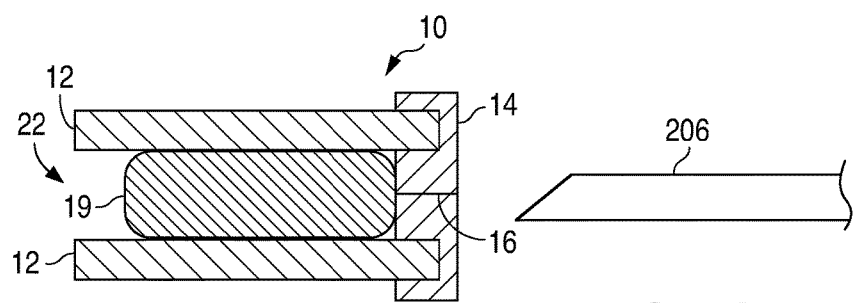
FIG. 1C is a side cross-sectional view of the shunt showing the needle withdrawn from the shunt and showing autonomous closure of the aperture.
Figure 2:
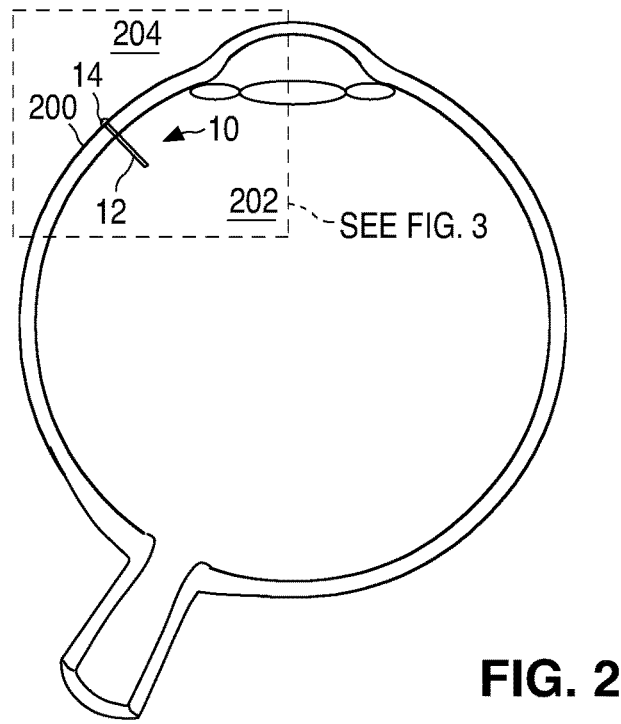
FIG. 2 is a cross-sectional view of a human eye showing the shunt implanted through the sclera.
Figure 3:
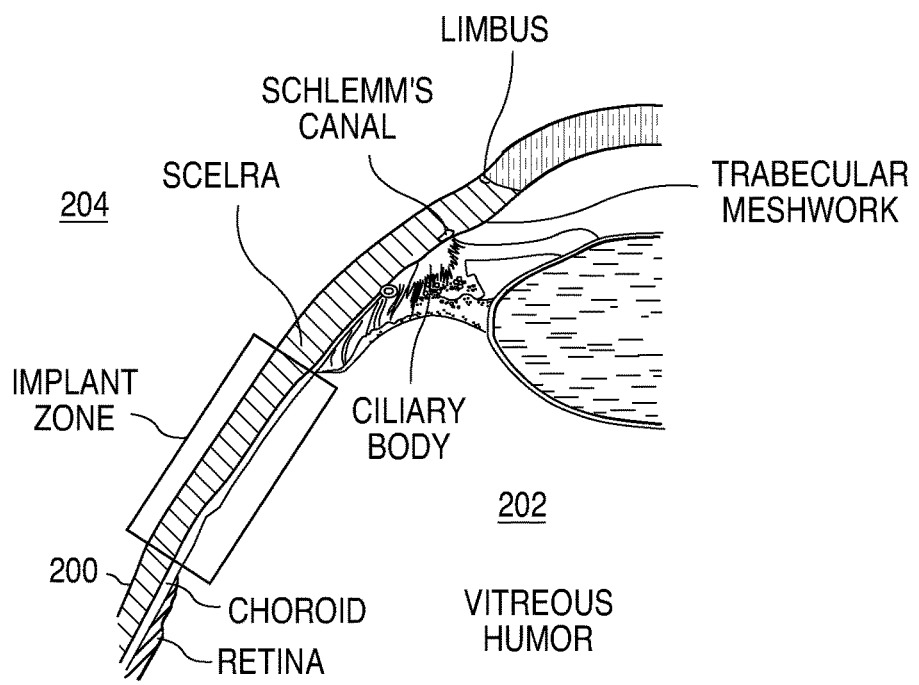
FIG. 3 is detailed cross-sectional view of the eye showing an exemplary implant zone for the shunt, the implant zone located between the ciliary body and the retina.

There is shown in FIGS. 1A-1C an exemplary ophthalmic shunt 10 for implantation into the sclera of the eye. FIG. 2 shows shunt 10 implanted through the sclera of eye 200. FIG. 3 shows an exemplary implant zone of eye 200 in which shunt 10 may be implanted. Shunt 10 may be implanted in another area of the eye.

Shunt 10 may be delivered using a small gauge needle to create a track in which the shunt is placed and inserted. Also, a laser may be used to create a track in which the shunt is placed and inserted.

Shunt 10 is configured to provide unlimited access to multiple injections of pharmaceutical and other therapeutic agents through shunt 10 and into the posterior segment of the eye while mitigating potential complications from repeated intraocular injections through the sclera in the absence of shunt 10. Shunt 10 forms a physical separation between intraocular space 202 and intraorbital space 204 while maintaining a conduit for insertion of needle 206 without repeated injury to the sclera. Needle 206 delivers therapeutic agent 19 to shunt 10.

Shunt 10 includes tube 12, septum 14, inlet aperture 20, and outlet aperture 22. Tube 12 functions as a compartment for holding a therapeutic agent. Septum 14, which covers inlet aperture 20, functions as a penetrable and re-sealable portal through which a therapeutic agent is introduced and reintroduced into tube 12. Tube 12 and septum 14 can be made of silicone elastomer or other non-degradable biomedical materials with well accepted biocompatibility. Tube 12 can be made by extruding a thermoplastic polymer in a relative biocompatible solvent, such as N-methylpyrrolidone, or in a solvent/water-based mixture. Other methods of making tubes, microtubes, needles and microneedles known in the art can be implemented for making tube 12.

Inlet aperture 20 is configured to receive needle 206 used to inject a therapeutic agent into shunt 10. Septum 14 is disposed adjacent to inlet aperture 20. Septum 14 forms a fluid seal within interior passageway 13 of tube 12. Passageway 13 serves as a cavity for temporarily holding the therapeutic agent. Septum 14 is configured to be penetrated by needle 206. Septum 14 is a partition configured for multiple needle penetrations performed at different times.

As shown in FIG. 1A, no aperture is present within septum 14 before the first insertion of needle 206 into septum 14. As shown in FIG. 1B, needle insertion creates aperture 16 through septum 14. As shown in FIG. 1C, septum 14 is configured to be self-healing. Self-healing means that when needle 206 is withdrawn, septum 14 autonomously closes aperture 16. Subsequent needle insertions may create a new aperture through septum 14 or pass through the aperture formed during a previous needle insertion. Every time a needle is withdrawn, the aperture closes autonomously to obstruct outward flow of internal eye fluid and therapeutic agent to intraorbital space 204.

Septum 14 can autonomously close aperture 16 by virtue of septum 14 being made of a self-healing material having sufficient elasticity to allow passage of the needle and sufficient resiliency to allow closure of aperture 16. Examples of self-healing materials include without limitation polymers or polymer composites with added healing agents, catalysts, or reactive agents that enhance mechanical performance and resistance to degradation and oxidation of the polymer or polymer composite. With use of a seal-healing material for septum 14, aperture 16 may either disappear or remain visible after removal of needle 206 from septum 14.

Figure 1D:
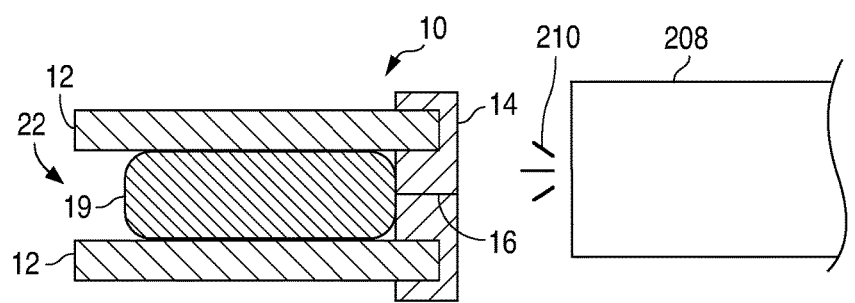
FIG. 1D is a side cross-sectional view of the shunt showing application of energy to induce repair of the septum and/or closure of the aperture.

As shown in FIG. 1D, external energy 210 source can be used to deliver energy 210 to induce healing or repair or closure of aperture 16. The application of energy 210 can be performed in addition to or as an alternatively to use of a self-healing material for septum 14. Examples of energy 210 include without limitation heat, ultraviolet radiation, an electrical field, or any combination thereof. Heat can induce further polymerization of the septum material to repair or close aperture 16. Septum 14 can be made of silicone elastomers with polymerization initiators that, with the application of heat, allow for living-type chemical reactions using silanolate end groups. Ultraviolet radiation can initiate free radical polymerization to repair or close aperture 16. Aperture 16 may either disappear or remain visible after application of energy 210.

In some embodiments, septum 14 is made of polymeric systems with built-in conductivity, such as organometallic polymers based on N-heterocyclic carbenes and transition metals as described by Kyle A. Williams et al. in "Towards electrically conductive self-healing materials" J. Royal Society of Interface, vol. 4, pp. 359-62 (2007), which is incorporated herein by reference in its entirety. The conductivity in polymeric materials can offer self-healing capabilities by an increase in electrical resistance from a drop in conductivity due to any structural damage, such as caused by needle 206. By connecting the damaged area of septum 14 to an electrical source, a voltage bias can generate localized heat at the structural damage, such as aperture 16, which then repairs septum 14 back to its original state (or near its original state) at low resistance and high current situation.

External surface 26 of tube 12 may include structural features or an adhesive coating that prevents shunt 10 from moving relative to eye 200 or otherwise becoming dislodged from its desired position and orientation. In addition or alternatively, an adhesive may be applied after shunt 10 is placed in the desired position and orientation in order to bond external surface 26 to the sclera or other structure of eye 200.

As shown by the side cross-sectional view of tube 12 in FIG. 1A, tube 12 is linear and has internal passageway 13 of constant size across longitudinal axis 27. In other embodiments of the invention, tube 12 can be non-linear so as to form an arc between proximal end 21 and distal end 23. Also, tube 12 can include one or more bends.

As shown by the end view of distal end 23 of tube 12 in FIG. 1A, tube 12 has a circular wall that forms the sides of tube 12. In other embodiments of the invention, tube 12 can have walls that are non-circular, such as elliptical or polygonal.

Figure 4:
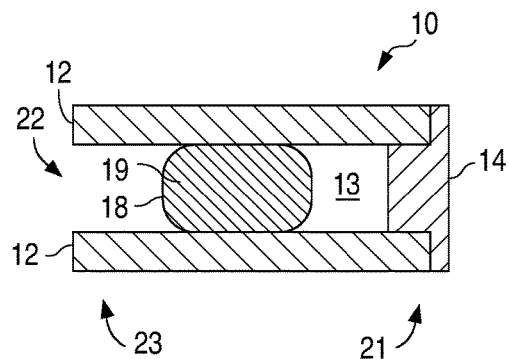
FIG. 4 is side cross-sectional view of a shunt showing a tube and a plug of therapeutic agent material contained in the tube.

As shown in FIG. 4, shunt 10 can include a composition or plug 18. Plug 18 may be solid, semi-solid, liquid, or a gel. Plug 18 includes therapeutic agent 19 which is released over a period of time through outlet aperture 22 and into intraocular space 202. In addition to therapeutic agent 19, plug 18 optionally includes an excipient, hydrophobic polymer, hydrogel, any combination thereof, and other materials.

In some embodiments, plug 18 can be native to shunt 10. Native means that plug 18 is already present in shunt 10 before implantation of shunt 10 into the eye, and that injection of plug material into shunt 10 is optional and not required.

In some embodiments, plug 18 is not native to shunt 10. That is, plug 18 is not present in shunt 10 before implantation of shunt 10 into the eye, and injection of plug material into shunt 10 can be performed after implantation.

Release of therapeutic agent 19 out of shunt 10 can be rapid or sustained. Rapid release refers to release in the order of hours or days. For example, rapid release refers to release over a period of time from an hour to days. Sustained release refers to release in the order of days or months. For example, sustained release refers to release over a period of time from days to months. Control of the length of time over which therapeutic agent 19 is released from shunt 10 can be accomplished by appropriate selection of material for plug 18.

For rapid release of therapeutic agent 19, plug 18 may include a combination of therapeutic agent 19 and a water soluble excipient. Examples of water soluble excipients include without limitation polyvinyl pyrrolidone (PVP) and a cellulosic.

In some embodiments, therapeutic agent 19 without an excipient is introduced into and carried by shunt 10 for release into intraocular space 202.

For sustained release of therapeutic agent 19, plug 18 may include a combination of therapeutic agent 19 and hydrophobic polymers or hydrogels. Hydrophobic polymers may form a matrix in which a therapeutic agent, such as a small molecule drug, is contained and released over a period of time. Examples of hydrophobic polymers include without limitation poly-DL-lactide (PDLLA), poly(vinylidene fluoride-co-hexafluoropropene (PVDF-HFP), poly(lactic-co-glycolic acid) (PLGA), poly(L-lactide-co-epsilon-caprolactone) (PLC), and PLGA-PEG block copolymers. PEG is an acronym for poly(ethylene glycol). A hydrogel may form a matrix in which a therapeutic agent, such as larger molecular-weight biologics can be contained and released over time. Examples of hydrogels include without limitation polyvinyl pyrrolidone (PVP), PEG, and biopolymers. A hydrogel may be introduced into shunt 10 as a liquid, and then become a gel after a period of time in shunt 10.

In some embodiments, therapeutic agent 19 without a polymer or hydrogel is introduced into and carried by shunt 10 for release into intraocular space 202.

In any of the embodiments above and below, shunt 10 may be loaded with therapeutic agent 19 with or without therapeutic agent 19 being encapsulated in, combined with, or contained within a hydrophobic polymer, hydrogel, or excipient.

Figure 5:
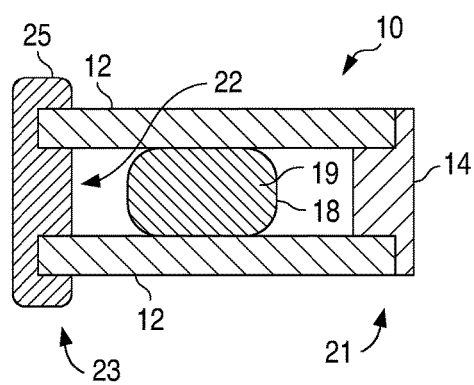
FIG. 5 is side cross-sectional view of a shunt showing a tube containing a plug of therapeutic agent material, the tube covered at opposite ends by a septum and a permeable membrane.

As shown in FIG. 5, shunt 10 can include membrane 25 attached to tube 12 and covering outlet aperture 22 of tube 12. Membrane 25 is made of a material that allows therapeutic agent 19 within tube 12 to permeate through membrane 25. Control of the length of time over which therapeutic agent 19 is released from shunt 10 can be accomplished by appropriate selection of material for membrane 25. Drug permeable membranes known in the art may be implemented.

In FIGS. 1A-1D, septum 14 is disposed partially inside of tube 12 and disposed adjacent to inlet aperture 20. In other embodiments, septum 14 is not disposed inside of tube 12 and is attached to proximal end 21 of tube 12.

In any of the embodiments above and below, tube 12 can include two or more septums, any number of which can be located inside of tube 12 and any number of which can be located outside of tube 12 to form additional embodiments.

Figure 6:
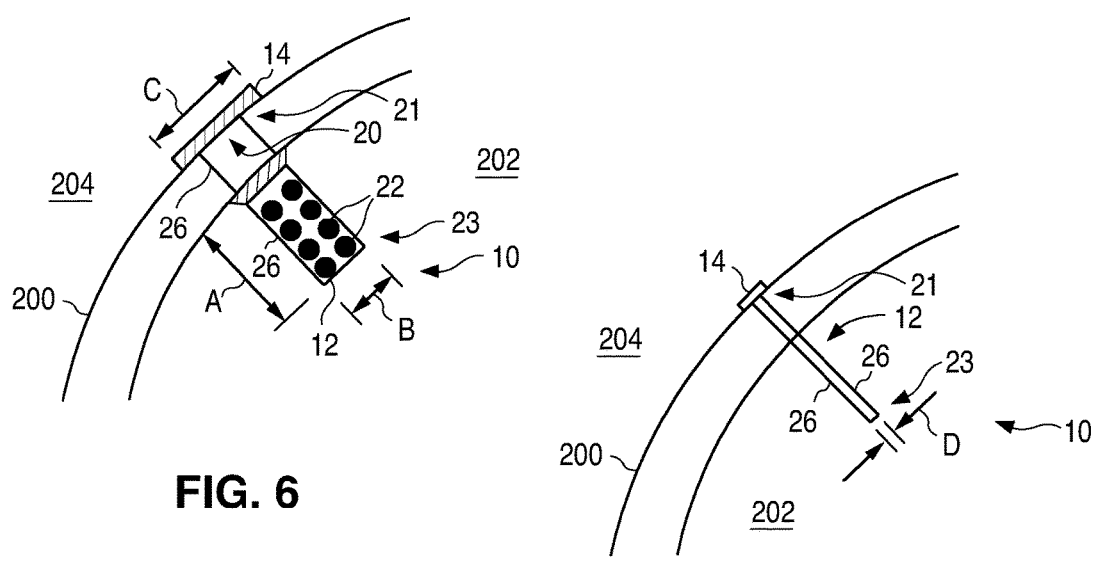
FIG. 6 is a cross-sectional view of a shunt implanted in an eye, showing a plurality of outlet apertures for releasing a therapeutic agent into the eye.

Shunt 10 is configured as shown in FIG. 6 in some exemplary embodiments of the invention. Septum 14 is in the form of a disk. Septum 14 is disposed outside of tube 12 and covers inlet aperture 20 of tube 12. Septum 14 is fixed to proximal end 21 of tube 12. Septum 14 protrudes radially outward from exterior surface 26 of tube 12. Septum 14 is disposed outside of intraocular space 202 and is optionally configured to inhibit shunt 10 from entering further into eye 200, such as when a needle is being pushed into septum 14. Shunt 10 includes ring 24 disposed around exterior surface 26. Tube 12 extends through ring 24. Ring 24 is fixed at an intermediate position between the proximal and distal ends of tube 12. Ring 24 is disposed within intraocular space 202. Ring 24 protrudes radially outward from exterior surface 26 and is optionally configured to inhibit shunt 10 from dislodging from eye 200, such as when a needle is being pulled out of septum 14. Optionally, outlet apertures 22 are covered by the permeable membrane discussed for FIG. 5.

Ring 24 can be made of a rigid material, semi-rigid material, or resilient materials. Ring can be made of the same material as septum 14.

The overall axial length of tube 12 is measured from proximal end 21 to distal end 23. In FIG. 6, the overall axial length of tube 12 is 1.5 mm to 5.5 mm, or from 1.5 mm to 3 mm, or from 3 mm to 5.5 mm. Tube 12 can protrude into intraocular space 202 by distance A from 1 mm to 5 mm, or from 1 mm to 3 mm, or from 3 mm to 5 mm. To minimize obstruction of eyesight, the overall axial length of tube 12 can be 0.5 mm to 2 mm in some embodiments of the invention.

In some embodiments, outer diameter B of tube 12 can be from about 0.4 mm to 5 mm, 0.4 mm to 2 mm, or 2 mm to 5 mm. Outer diameter C of septum 14 can be from 0.5 mm to 6 mm, or from 0.5 mm to 3 mm, or from 3 mm to 6 mm. These values for overall axial length, distance A, outer diameter B, and/or outer diameter C can be implemented in any of the embodiments above and below to form additional embodiments.

In any of the embodiments above and below, other values may be implemented for the overall axial length, distance A, outer diameter B, and outer diameter C to form additional embodiments.

The length of time over which a therapeutic agent is released from shunt 10 can be controlled by the structure of tube 12 of shunt 10. For example, the diameter of one or more outlet apertures 22 of tube 12 can be selected to deliver a therapeutic agent over a desired length of time. A larger size for aperture 22 can allow for faster release of a therapeutic agent. As a further example, the number of apertures 22 can be selected to deliver a therapeutic agent over a desired length of time. A greater number of apertures 22 can allow for faster release of a therapeutic agent. One or more apertures 22 can be located at the distal end of tube 12 as shown in FIG. 1, at sides of tube 12 as shown in FIG. 5, or both the distal end and sides of tube 12.

In any of the embodiments above and below, shunt 10 or conduit 28 (FIG. 9) may either exclude or include ring 24 as described for FIG. 6 to form one or more additional embodiments.

Figure 7:
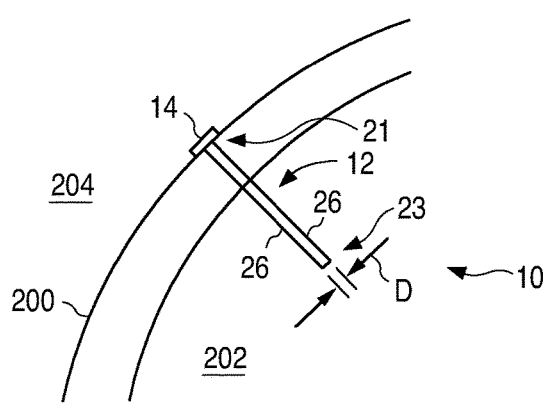
FIG. 7 is a cross-sectional view of a shunt implanted in an eye, showing a thin, elongate tube for carrying and releasing a therapeutic agent into the eye.

Shunt 10 is configured as shown in FIG. 7 in some exemplary embodiments of the invention. Tube 12 is kept to a minimal, slim profile in order to facilitate a minimally invasive insertion procedure for implanting shunt 10 in eye 200. In FIG. 7, diameter D of tube 12 is from 0.1 mm to 2 mm, or from 0.1 mm to 1 mm, or from 1 mm to 2 mm. These values for diameter D can be implemented in any of the embodiments above and below to form additional embodiments. For all embodiments, other values for diameter D may be implemented.

In FIG. 7, a therapeutic agent within tube 12 is released through one or more outlet apertures at distal end 23 of tube 12 and/or exterior side surface 26 of tube 12. Optionally, the outlet apertures are covered by the membrane discussed for FIG. 5. Optionally, tube 12 does not expand or swell after a therapeutic agent is injected through septum 14 and into tube 12. Alternatively, tube 12 is configured to expand after a therapeutic agent is injected through septum 14 and into tube 12. Expansion may prevent outward movement of shunt 10 from eye 200.

In some embodiments, tube 12 is be made of an elastic polymer material that does not allow the therapeutic agent to permeate through tube 12, and tube 12 expands as a result of injection of a therapeutic agent through septum 14.

In other embodiments, tube 12 is be made of an elastic polymer material that allows the therapeutic agent to permeate slowly through tube 12, and tube 12 expands as a result of injection of a therapeutic agent through septum 14.

Figure 8:
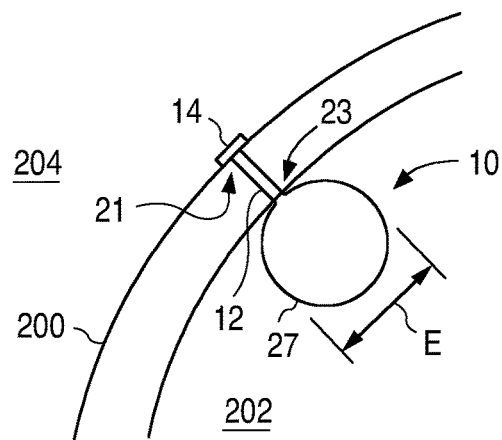
FIG. 8 is a cross-sectional view of a shunt implanted in an eye, showing a tube passing through the sclera and attached to an inflatable, permeable balloon for carrying and releasing a therapeutic agent into the eye.

Shunt 10 is configured as shown in FIG. 8 in some exemplary embodiments of the invention. Shunt 10 includes balloon 27 fixed to distal end 23 of tube 12. Balloon 27 is configured to expand as a result of injection of a therapeutic agent through septum 14. The injected therapeutic agent flows from tube 12 and into balloon 27. Balloon 27 is made of a material that allows the therapeutic agent to permeate through the walls of balloon 27. The balloon material can be elastic to allow for expansion. Tube 12 can be made of the same material as balloon 27 or a different material. For example, tube 12 can be made of a material that is more rigid or less elastic than the balloon material to inhibit expansion of eye tissue surrounding tube 12. Also, tube 12 can be made of a material that is non-permeable with respect to the therapeutic agent to inhibit release of the therapeutic material to intraorbital space 204.

In some embodiments, balloon 27 in its expanded state can have an outer diameter E from 1 mm to 5 mm, or from 1 mm to 3 mm, or from 3 mm to 5 mm. For all embodiments, these and other values for diameter E may be implemented.

In the forgoing embodiments, tube 12 or balloon 27 functions as a storage reservoir for holding a therapeutic agent in intraocular space 202. In other embodiments, a therapeutic agent is held in a storage reservoir outside of intraocular space 202.

Figure 9:
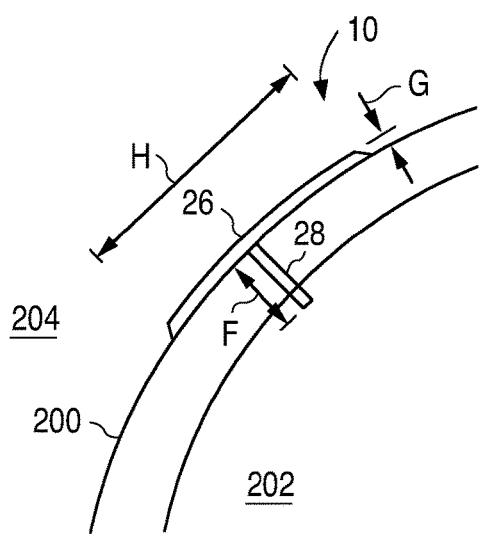
FIG. 9 is a cross-sectional view of a shunt implanted in an eye, showing a reservoir for carrying a therapeutic agent and connected to a conduit for transporting the therapeutic agent from the reservoir to interior of the eye.

Shunt 10 is configured as shown in FIG. 9 in some exemplary embodiments of the invention. Shunt 10 includes external reservoir 26 fixed to the proximal end of conduit 28. Conduit 28 is configured to transport a therapeutic agent from reservoir 26. Reservoir 26 is disposed outside of intraocular space 202, and can be positioned between the sclera and the Tenon's capsule which surrounds eye 200. The Tenon's capsule is a thin membrane which envelops the eyeball. Reservoir 26 is configured to carry a therapeutic agent and release the therapeutic agent to conduit 28, from which the therapeutic agent is released into intraocular space 202. Conduit 28 need not have an outlet aperture. Conduit 28 can be a made of material configured to allow the therapeutic agent in reservoir 26 to permeate through conduit 28 and be released into intraocular space 202. Conduit 28 can be either non-hollow or hollow. For embodiments in which conduit 28 is hollow, conduit 28 can be sized, shaped, and configured with one or more outlet apertures as discussed above for tube 12.

In some embodiments, reservoir 26 is a hollow structure having a round foot print and flat elevation shape. Reservoir 26 may be soft and flexible to allow it to bend and conform to the curvature of eye 200. Reservoir 26 can be configured to swell in size when a therapeutic agent encapsulated in hydrogel is introduced into reservoir 26.

In some embodiments, as the hydrogel swells and degrades over time, the therapeutic agent will slowly over time be pushed out of reservoir 26 through conduit 28. After sufficient degradation, diffusion of the therapeutic agent through conduit 28 will be the dominant way the therapeutic agent is transported into intraocular space 202. Reservoir 26 can be made of any one or a combination of elastic polymers, including without limitation polypropylene, silicone and any of the self-healing materials described herein. Reservoir 26 may comprise a hollow structure that can be filled by injection of therapeutic agent encapsulated inside a hydrogel and then swell in size.

Injection of a therapeutic agent into reservoir 26 can be performed before or after reservoir 26 is applied on eye 200. Reservoir 26 can be applied on eye 200 using a method similar to any method used for a scleral patch known in the art. Reservoir 26 is optionally disposable and configured to be removed from eye 200 and replaced with another reservoir 26 as needed.

In some embodiments, reservoir 26 has thickness G from 0.5 mm to 2 mm, 0.5 to 1 mm, or 1 mm to 2 mm. Reservoir 26 has foot print diameter H from 10 mm to 24 mm, from 10 mm to 15 mm, or from 15 mm to 24 mm. In some embodiments, reservoir 26 has a surface area from 100 mm^2 to 500 mm^2, from 100 mm^2 to 300 mm^2, or from 300 mm^2 to 500 mm^2. Other values for thickness G and diameter H may be implemented. These and other values for thickness G and surface area can be implemented for septum 14 in any of the embodiments above and below to form additional embodiments.

Shunt 10 may optionally include a safety feature configured to prevent a needle from being inserted too far which could risk damaging the lens, retina, or other parts of the eye.

Figure 10A:
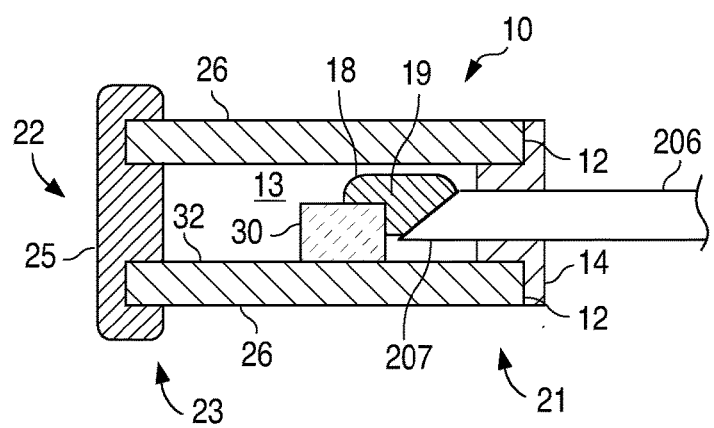
FIGS. 10A and 10B are side cross-sectional views of shunts, showing stop features to limit travel of a needle within the shunts.
Figure 10B:
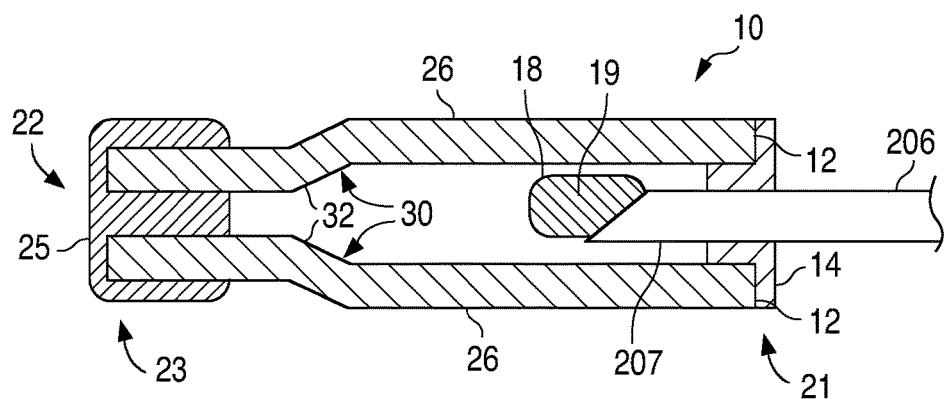

Shunt 10 is configured as shown in FIGS. 10A and 10B in some exemplary embodiments of the invention. Shunt 10 includes stop feature 30. Stop feature 30 is a safety feature configured to prevent needle 206 from being inserted too far through tube 12 which could risk damaging the lens, retina, or other parts of the eye. Stop feature 30 stops tip 207 of needle 206 from exiting distal end 23 of tube 12. Stop feature 30 creates a constriction of interior passageway 13 of tube 12. The constriction reduces the diameter of internal passageway 13 to a size that is smaller than the commonly used ophthalmic injection needle gauge, and thereby blocks passage of tip 27 of needle 206 while allowing passage of therapeutic agent 19 injected by the needle. Common ophthalmic needle gauges for intraocular injections are 27-, 30-, and 31-gauge needles, although others may be used.

In some embodiments, inlet aperture 20 has a diameter capable of receiving needle 206 having a gauge of 27, 30, 31, or from 27 to 31. Stop feature 30 creates a constriction of interior passageway 13 of tube 12 that prevents needle 206 having a gauge of 27, 30, 31, or from 27 to 31 from passing through outlet aperture 22.

In some embodiments, inlet aperture 20 has a diameter greater than 0.45 mm, or greater than 0.25 mm. Stop feature 30 creates a constriction of interior passageway 13 of tube 12 at which passageway 13 has a diameter less than 0.45 mm, or less than 0.25 mm.

In FIG. 10A, stop feature 30 is a piece of material fixed onto tube 12 at a position between septum 14 and distal end 23 of tube 12. The piece of material protrudes radially inward from internal surface 32 of tube 12.

In FIG. 10B, stop feature 30 is a radially inward bend of the sides of tube 12. A portion of an internal surface 32 of tube 12 protrudes radially inward. The inward bend is located at a position between septum 14 and distal end 23 of tube 12.

In any of the embodiments above and below, tube 12 or conduit 28 may either exclude or include stop feature 30 as described in FIG. 10A and/or 10B to form one or more additional embodiments.

In combination with or as an alternative to the stop feature 30 on shunt 10, an injection needle can be used which includes a safety feature that engages shunt 10 to prevent the needle from being inserted too far which could risk damaging the lens, retina, or other parts of the eye.

Figure 11:
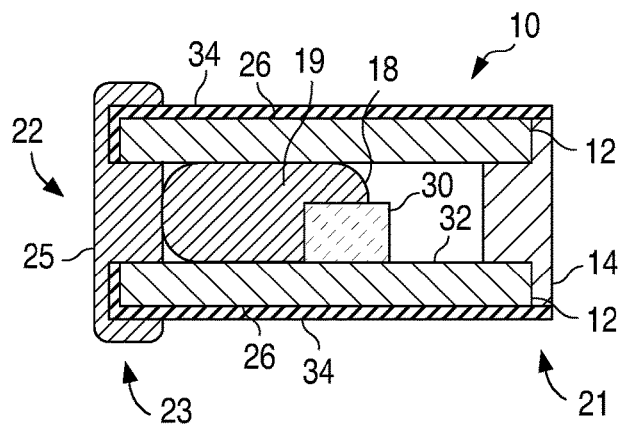
FIG. 11 is a side cross-sectional view of a shunt showing a tube and a coating on the tube.

Shunt 10 is configured as shown in FIG. 11 in some exemplary embodiments of the invention. Coating 34 is disposed on outer surface 26 of tube 12 as shown in FIG. 11 or on both outer surface 26 and internal surface 32 of tube 12. In addition or alternatively, coating 34 can be disposed on septum 14.

Coating 34 can include an antibiotic drug and/or silver ions to prevent infection. Coating 34 can include extracellular matrix materials, such as biocompatible polymers or hydrogels, that can promote adhesion and stability of shunt 10 at the trans-scleral implant site. Extracellular matrix materials can be synthetic materials or naturally-derived materials. Examples of synthetic materials include without limitation cross-linked polyethylene glycol and polylactide-co-glycolide. Examples of naturally-derived materials include without limitation alginate and collagen.

In other embodiments, a coating that promotes adhesion and stability may be applied only to a portion of outer surface 26 adjacent to proximal end 21, there being no such coating on a portion of outer surface 26 adjacent to distal end 23.

In any of the embodiments above and below, any one or more of tube 12, septum 14, balloon 27, conduit 28, and reservoir 26 may either exclude or include the coating and coating variations described above in connection with FIG. 11 to form one or more additional embodiments of the invention. The coating can be applied by spray coating, direct fluid application, and/or dip coating.

In any of the embodiments above and below, shunt 10 may either exclude or include outlet apertures 22 formed through sides of tube 12 or conduit 28 in order to form one or more additional embodiments.

In any of the embodiments above and below, the therapeutic agent that is used includes any one or a combination of two or more of the therapeutic agents described below.

Suitable therapeutic agents include those that improve on late complications after tube-shunt surgery, such as therapeutic agents that reduce scar tissue and prevent infection.

Suitable therapeutic agents include without limitation prostaglandin analogs (such as Xalatan (R), Lumigan (R), and Travatan Z (R)), beta blockers (such as timolol), alpha antagonists (such as Alphagan (R) P, and iopidine), carbonic anhydrase inhibitors, combinations of these agents, corticosteroids, dexamethasone, mTOR inhibitors, anti-VEGF antibodies, Avastin (R), Lucentis (R), Eylea (R) (VEGF receptor). VEGF is an acronym for vascular endothelial growth factor. Prostaglandin analogs, beta blockers, alpha antagonists, and carbonic anhydrase inhibitors may serve to both treat high intraocular pressure (TOP) and prevent unwanted complication of IOP increase due to repeat intraocular injections. Antinflamatory and immunosuppressant agents, such as corticosteroids, dexamethasone, and mTOR inhibitors may serve to treat multiple eye diseases including uveitis.

Suitable therapeutic agents also include without limitation miotic agents, such as pilocarpine, may serve to increase outflow of aqueous humor of the eye.

Suitable therapeutic agents also include without limitation antibiotics such as besifloxacin, ciprofloxacin, moxifloxacin, and azithromycin, any of which may serve to inhibit microbiologic grown due to repeated intraocular injections.

Suitable therapeutic agents also include without limitation paclitaxel, anti-VEGF antibodies, and other anti-VEGF biologics for the treatment of retinal eye diseases, such as wet, age-related macular degeneration, diabetic retinopathy, and macular edema. These therapeutic agents and others may be used for sustained release.

In any of the embodiments above and below, tube 12 or conduit 28 can be made from non-degradable biomedical materials including without limitation silicone elastomers, polypropylene, poly(methyl methacrylate (PMMA), acrylic polymers, poly(2-hydroxyethyl methacrylate (PHEMA), gold, platinum, polyurethane, polyurethane urea, polyether block amide (for example Pebax (R)), and polyamide.

Figure 12:
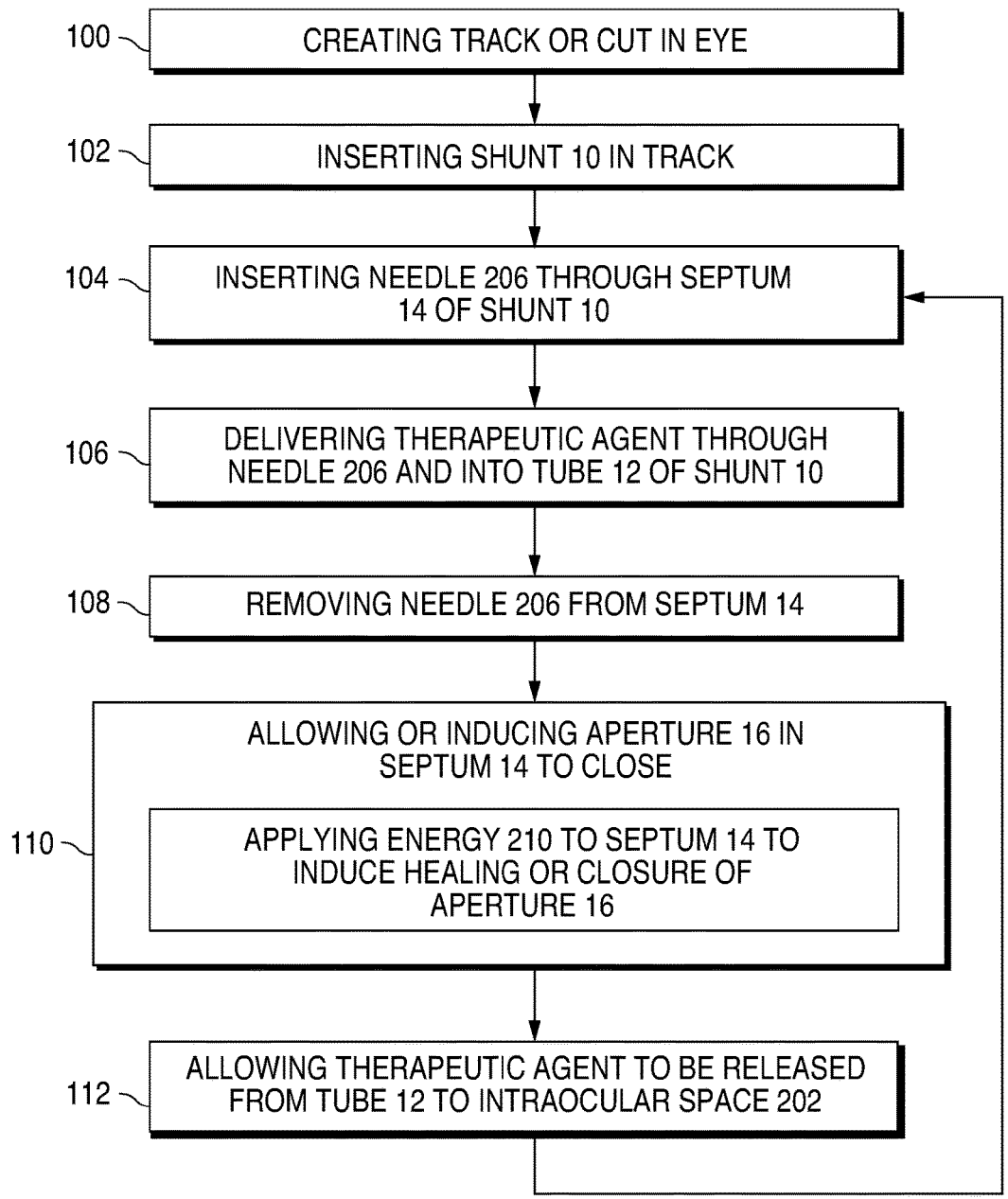
FIG. 12 is a diagram showing an exemplary method.

FIG. 12 shows an exemplary method of the present invention. In block 100, create a trans-scleral track or cut in the eye of a person or animal. This can be accomplished using a sharp implement or by using a laser. The track or cut can be made in the implantation zone shown in FIG. 3 or in another region of the eye. In block 102, insert shunt 10 in the track or cut. In block 104, insert needle 206 through septum 14 of shunt 10. Needle 206 can be previously or later connected to a container of therapeutic agent. Needle 206 can be part of a plunger type injector that contains a therapeutic agent. In block 106, deliver the therapeutic agent through needle 206 and into tube 12 of shunt 10. This can be accomplished by pressing the plunger of the plunger type injector. In block 108, remove needle 206 from septum 14. In block 110, allow or induce aperture 16 in septum 14 to close, which optionally includes application of energy 210 to septum 14 to induce healing or closure of aperture 16. Energy 210 can be heat, ultraviolet radiation, an electric field, or any combination thereof from energy source 208. Aperture 16 may close without any active application of energy. In block 112, allow the therapeutic agent to be released from tube 12 to the intraocular space of the eye. Thereafter, blocks 104-112 can optionally be repeated to load shunt 10 with the same or different therapeutic agent.

In some embodiments, shunt 10 already contains a therapeutic agent before shunt 10 is inserted in the track formed in the eye. The therapeutic agent may be allowed to be released from shunt 10 into the intraocular space before blocks 104 to 110 are performed to load shunt 10 with the same therapeutic agent or a different therapeutic agent. Blocks 104 to 110 are optional and may not be performed in other embodiments.

Figure 13:
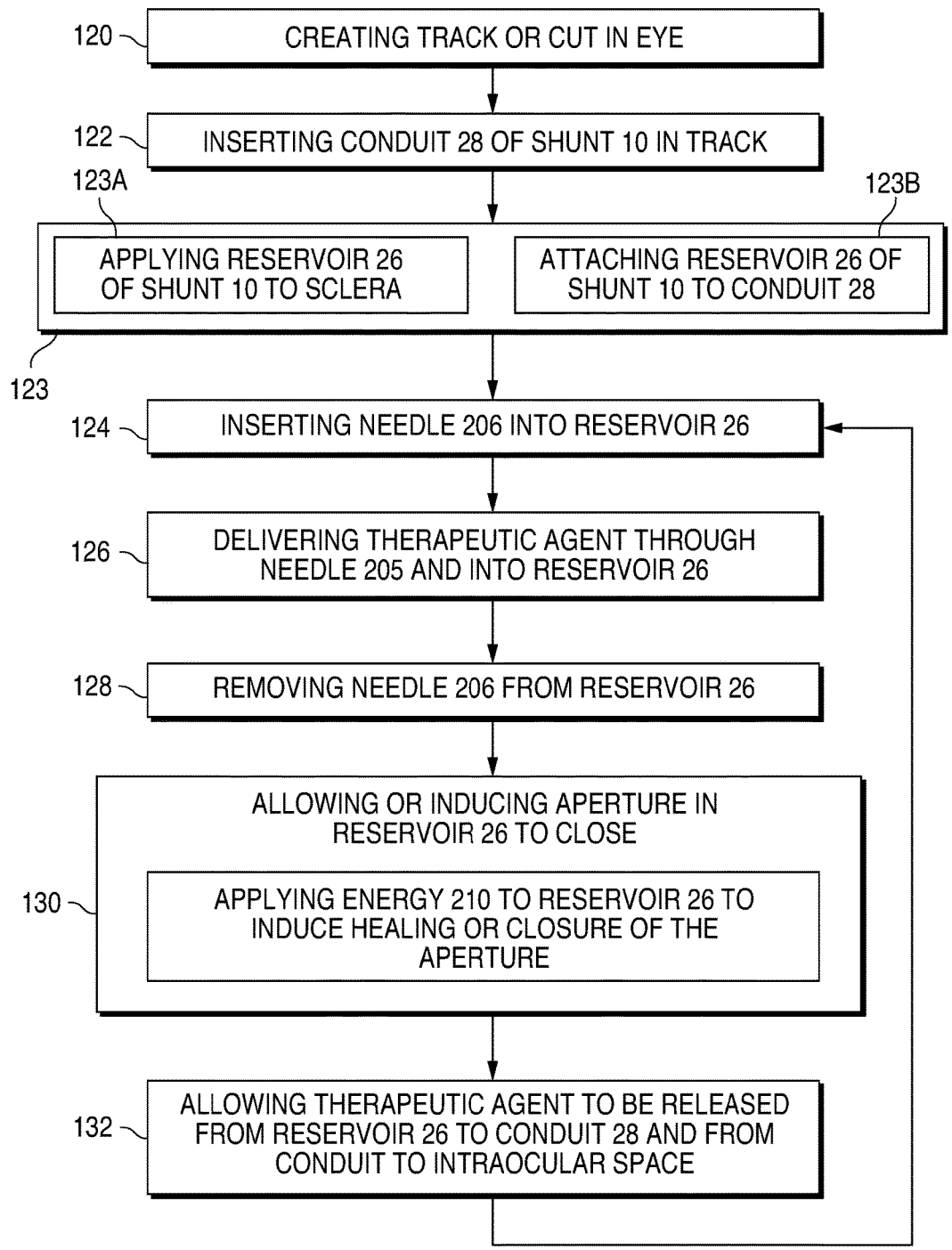
FIG. 13 is a diagram showing an exemplary method.

FIG. 13 shows an exemplary method of the present invention. In block 120, create a trans-scleral track or cut in the eye of a person or animal. This can be accomplished using a sharp implement or by using a laser. The track or cut can be made in the implantation zone shown in FIG. 3 or in another region of the eye. In block 122, insert conduit 28 in the track or cut.

In some embodiments, conduit 28 is not attached to reservoir 26 before block 120. In such cases, inserting of conduit 28 in the track or cut is followed by performance of block 123, which includes applying reservoir 26 to the sclera and attaching reservoir 26 to conduit 28.

In some embodiments, conduit 28 is already attached to reservoir 26 before block 120. In such cases, insertion of conduit 28 of shunt 10 in the track or cut is followed by or performed at the same time as application of reservoir 26 to the sclera of the eye in block 123A. Block 123B is not performed since reservoir 26 was previously attached to conduit 28.

Next in block 124, insert needle 206 into reservoir 26. Needle 206 forms an aperture in reservoir 26 or passes through an existing aperture. Needle 206 can be previously or later connected to a container of therapeutic agent. Needle 206 can be part of a plunger type injector that contains a therapeutic agent. In block 126, deliver the therapeutic agent through needle 206 and into reservoir 26. This can be accomplished by pressing the plunger of the plunger type injector. In block 128, remove needle 206 from reservoir 26. In block 130, allow or induce the aperture in reservoir to close, which optionally includes application of energy 210 to reservoir 208 to induce healing or closure of the aperture. Energy 210 can be heat, ultraviolet radiation, an electric field, or any combination thereof from energy source 208. The aperture may close without any active application of energy. In block 132, allow the therapeutic agent to be released from reservoir 26 to conduit 28 and from conduit 28 to the intraocular space of the eye. Thereafter, blocks 124-132 can optionally be repeated to load reservoir 26 with the same or different therapeutic agent.

In some embodiments, reservoir 26 already contains a therapeutic agent before block 122. The therapeutic agent may be allowed to be released from reservoir 26 before blocks 124 to 130 are performed to load reservoir 26 with the same therapeutic agent or a different therapeutic agent. Blocks 124 to 130 are optional and may not be performed in other embodiments.

The methods described above may be used to treat diseases of the eye, including without limitation high intraocular pressure, uveitis, and retinal eye diseases such as wet age-related macular degeneration, diabetic retinopathy, and macular edema. The methods describe above may also be used to increase the outflow of aqueous humor and prevent infection.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. An implantable ophthalmic shunt comprising:
   a tube, there being an inlet aperture at an end of the tube; and
   a septum covering the inlet aperture of the tube, the septum forming a resilient seal against fluid flow, the septum configured to be pierced by a needle, wherein the septum is made of a material that includes a polymerization initiator that is activated by application of energy to the septum to seal a hole in the septum caused by needle insertion, wherein the polymerization initiator is activated by ultraviolet radiation,
   wherein the tube has no outlet aperture for releasing material out of the tube.

2. The implantable ophthalmic shunt of claim 1, wherein the septum is configured to autonomously close an aperture formed by a needle having pierced the septum and having been withdrawn from the septum.

3. The implantable ophthalmic shunt of claim 1, wherein the septum is made of a silicone elastomer.

4. The implantable ophthalmic shunt of claim 1, wherein the polymerization initiator is activated by application of heat, ultraviolet radiation, an electric field, or a combination thereof to the septum.

5. The implantable ophthalmic shunt of claim 1, wherein the tube is configured to swell or expand with introduction of a therapeutic agent into the tube.

6. The implantable ophthalmic shunt of claim 1, wherein the tube has a cavity containing a composition including a therapeutic agent.

7. The implantable ophthalmic shunt of claim 6, wherein the composition further includes any of an excipient, hydrophobic polymer, hydrogel, and a combination of two or more thereof.

8. The implantable ophthalmic shunt of claim 6, wherein the tube is made of a permeable material through which the therapeutic agent permeates.

9. The implantable ophthalmic shunt of claim 1, further comprising a coating over an outer surface of the tube.

10. The implantable ophthalmic shunt of claim 9, wherein the coating is configured to adhere to eye tissue.

11. The implantable ophthalmic shunt of claim 9, wherein the coating includes a substance selected from the group consisting of an antibiotic, silver ions, extracellular matrix material, and a combination of two or more thereof.

12. The implantable ophthalmic shunt of claim 9, wherein the coating includes one or both of cross-linked polyethylene glycol and polylactide-co-glycolide.

13. The implantable ophthalmic shunt of claim 1, further comprising a ring disposed between a proximal end of the tube and a distal end of the tube, the ring extending circumferentially around an exterior surface of the tube and protruding radially outward from the exterior surface.

14. The implantable ophthalmic shunt of claim 1, wherein the septum protrudes radially outward from the tube.

15. The implantable ophthalmic shunt of claim 1, further comprising a balloon attached to the tube.

16. The implantable ophthalmic shunt of claim 1, wherein the tube includes an interior passageway, and a stop feature within the tube constricts the interior passageway to block passage of a needle.

17. A method comprising:
   introducing a therapeutic agent through a septum covering an inlet aperture formed at an end of a tube of an ophthalmic shunt implanted through the sclera of an eye, wherein the tube has no outlet aperture for releasing material out of the tube; and
   allowing the therapeutic agent to permeate through the tube and into the eye,
   wherein introducing the therapeutic agent through the septum includes piercing the septum with a needle and injecting the therapeutic agent through the needle,
   after piercing the septum with the needle, activating a polymerization initiator in the septum to seal a hole formed by the needle in the septum,
   wherein activating the polymerization initiator includes applying ultraviolet radiation to the septum to seal a hole formed by the needle in the septum.

18. The method of claim 17, wherein the piercing of the septum with the needle includes moving the needle through an interior passageway of the tube, and the movement of the needle through an interior passageway is limited by a constriction in the interior passageway.

19. An implantable ophthalmic shunt comprising:
   a tube, there being an inlet aperture at an end of the tube; and
   a septum covering the inlet aperture of the tube, the septum forming a resilient seal against fluid flow, the septum configured to be pierced by a needle, wherein the septum is made of a material that includes a polymerization initiator that is activated by application of energy to the septum to seal a hole in the septum caused by needle insertion, wherein the polymerization initiator is activated by an electric field,
   wherein the tube has no outlet aperture for releasing material out of the tube.

20. A method comprising:
   introducing a therapeutic agent through a septum covering an inlet aperture formed at an end of a tube of an ophthalmic shunt implanted through the sclera of an eye, wherein the tube has no outlet aperture for releasing material out of the tube; and allowing the therapeutic agent to permeate through the tube and into the eye, wherein introducing the therapeutic agent through the septum includes piercing the septum with a needle and injecting the therapeutic agent through the needle, after piercing the septum with the needle, activating a polymerization initiator in the septum to seal a hole formed by the needle in the septum, wherein activating the polymerization initiator includes applying an electric field to the septum to seal a hole formed by the needle in the septum.

* * * * *